United States Patent [19]

Wilson et al.

[11] Patent Number: 4,530,789

[45] Date of Patent: Jul. 23, 1985

[54] SUBVALENT HALIDE COMPOUNDS TETRASELENOFULVALENE AND TETRATHIOFULVALENE SUBVALENT HALIDES

[75] Inventors: James D. Wilson, University City; Malcolm G. Miles, St. Louis, both of Mo.

[73] Assignee: Monsanto Company, St. Louis, Mo.

[21] Appl. No.: 85,351

[22] Filed: Oct. 16, 1979

Related U.S. Application Data

[63] Continuation-in-part of Ser. No. 536,147, Dec. 24, 1974, abandoned.

[51] Int. Cl.$^3$ ................. C07D 421/04; C07D 409/02
[52] U.S. Cl. .................................. 260/239 R; 549/59
[58] Field of Search ...................... 260/239 R; 549/59

[56] References Cited

U.S. PATENT DOCUMENTS

| | | | |
|---|---|---|---|
| 3,833,894 | 9/1974 | Aviram et al. | 340/173 R |
| 3,953,874 | 4/1976 | Aviram et al. | 357/8 |
| 4,028,346 | 6/1977 | Engler et al. | 260/239 R |

OTHER PUBLICATIONS

Coleman et al., "Physics Letters", 51A, pp. 412–414 (1975).
Daly et al., Chem. Abstr., 82, Abst. 178808a, (Abst. of Acta Crystallogr., Sect. B, 31, pp. 620 & 621 (1975).
Kaufmann et al., JACS, 98, pp. 1596 & 1597 (1976).

*Primary Examiner*—Richard L. Raymond
*Assistant Examiner*—D. B. Springer
*Attorney, Agent, or Firm*—Joseph D. Kennedy; James W. Williams, Jr.

[57] ABSTRACT

Subvalent organic halide compounds of variable, non-integral stoichiometry are described. Related subvalent double cation, halide compounds of variable non-integral stoichiometry are described where the double cation is comprised of an organic cation in combination with a single valent transition metal.

12 Claims, No Drawings

SUBVALENT HALIDE COMPOUNDS TETRASELENOFULVALENE AND TETRATHIOFULVALENE SUBVALENT HALIDES

This application is a continuation-in-part of application Ser. No. 536,147, filed Dec. 24, 1974, abandoned.

DESCRIPTION OF PRIOR ART

The prior art is replete with references to a wide variety of organo-halide compounds; however this chemistry is customarily taught and thought of in terms of stoichiometric compound formation. The term stoichiometric in this sense has the meaning that relative numbers of different atoms in a molecule can be specified as ratios of small integers. The existence of nonstoichiometric solid phases is recognized, particularly among transition metal oxides and sulfides. For example, in the case of the art-taught nonstoichiometric or subvalent rutile, the formula of the solid is given as $TiO_x$ where the relationship is defined approximately by x being greater than about 1.8 and less than 2.0. The physical and chemical properties of solids within this subvalent range of compositions differ substantially from the stoichiometric form of rutile, $TiO_2$.

The concept of valence is generally thought of by the art in integral terms; thus the term fails in its general use when compounds are subvalent or nonstoichiometric. In the example rutile ($TiO_{1.9}$), the titanium atoms are said to exhibit an average valence of $+3.8$, which is usually interpreted in terms of every fifth titanium atom as having an extra election. Another and perhaps more satisfactory art description of these subvalent solids is that the extra electrons are delocalized throughout the crystal.

Subvalent or nonstoichiometric solids of this kind are very rare among organic compounds except possibly among synthetic polymers whose composition can only be specified as $(M)_x$ where M is some monomer unit and x is some average, polymerization number; however these polymers are preferably regarded as solid solutions of the various molecules $(M)_x$.

This invention pertains to novel compositions of matter comprised of subvalent organic halide compounds. The novel compositions are characterized by organic cations singly or in combination with hydrogen or one-valent transition metal cations chemically coupled nonstoichiometrically with halide ions. For the purpose of this invention the expression "single valent transition metal cations" is defined to be interchangeable with the term "transition elements." Transition elements are those elements in which an inner electron shell, rather than an outer shell is partially filled. In the periodic table they include elements 21 through 30 (scandium through zinc), 39 through 48 (yttrium through cadmium), 57 through 80 (lanthanum through mercury) and 80 through 103 (actinium through lawrencium). They are all metals and most possess colored ions, variable valency, have a tendency to form complexes, and to have large magentic moments.

SUMMARY OF THE INVENTION

This invention pertains to subvalent organic halide compounds of variable nonintegral stoichiometry wherein the halide presence is nonstoichiometric in relationship to the organic cation or double cation comprised of an organic cation in combination with hydrogen or a single-valenttransition metal. Compositions according to the invention are comprised of subvalent organic halide compounds having the formula:

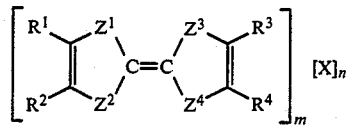

where m is an integer of one or more; n is positive number of at least about 0.001, is less than m and is such that the quotient n/m cannot generally be expressed as a ratio of small whole numbers ("small" in this context meaning five or less); $R^1$, $R^2$, $R^3$, $R^4$ are each independently selected from the group of hydrogen, an alkyl, alkenyl, or allyl group having from 1 to about 7 carbon atoms per group; $Z^1$, $Z^2$, $Z^3$, $Z^4$ are each independently selected from a Group VIA element; and Z is at least one of chlorine, iodine, or bromine. For the purposes of this invention, the term positive number shall be defined as any number such as an integer or part of an integer which is greater than zero, preferably defined as a number of at least 0.001. Related compositions according to the invention are comprised of double cation compounds of subvalent halides having the formula:

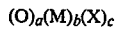

where (O) is the organic cation having the formula:

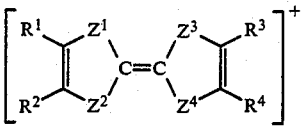

$R^1$, $R^2$, $R^3$, $R^4$ are each independently selected from the group of hydrogen, an alkyl or allyl group having from 1 to about 7 carbon atoms per group; $Z^1$, $Z^2$, $Z^3$, $Z^4$ are each independently selected from a Group VIA element; (M) is hydrogen or a single valent transition metal; (X) is at least one of chlorine, bromine, or iodine; a is an integer of one or more; b is a positive number of at least about 0.001; c is a positive number of at least about 0.001; and the integer a is greater than c-b.

DESCRIPTION OF PREFERRED EMBODIMENTS

In the above subvalent halide compounds it often happens that $Z^1$, $Z^2$, $Z^3$ and $Z^4$ in the organic cations are either all sulfur or all selenium, and that m is 1 and n is a positive number of from about 0.5 to about 0.9. The subvalent halide compounds are characterized by electrical conductivity which is greater, in fact generally markedly greater, than that of the corresponding compound with a 1:1 ratio of m to n, i.e. that of the stoichiometric halide compound. The electrical conductivity is a function of crystallographic phase. Different compositions can have different crystallographic phases, but there is a range of compositions having suitable crystallography for the desired higher electrical conductivity and the present invention includes subhalide compounds with compositions, i.e. m to n ratios, characterized by higher electrical conductivity. The compositions have electrical conductivity such as to be termed conductors, with room temperature conductivity generally being at least 75 ohm$^{-1}$ cm$^{-1}$, and usually 90 or more ohm$^{-1}$ cm$^{-1}$.

The considerations for the double cation compounds are similar to the above in that the compositions provide conductivity higher than that of the stoichiometric organic halide compounds and in the ranges of the subvalent compounds. In the double cation compounds the halide constituent is present in excess (molar basis) of the metal constituent, that is, c in the formula is greater than b. The amount of metal can vary, e.g. in ranges of 1–10% by weight. The double salt catio subvalent compounds can be formed by treatment of the organic moiety of the compound, e.g. tetrathifulvalene, with a halide salt, e.g. anhydrous cupric chloride, in a solvent, e.g. acetonitrile, with crystallization from the solvent by procedures such as cooling.

Organic cations of the above subvalent halide compounds can be selected from, for example, (tetrathiafulvalene)+, i.e., (TTF)+; (tetraselenofulvalene)+, i.e., (TSeF)+ and the like where the Z groups of the above formula are each independently selected from a Group VIA element and are other than all sulphur or selenium. In addition to any of the above compounds, any number of organic cations would be suitable according to the invention such as (2,5-cyclohexadiene-1,4-diylidine-bis-1,3-dithiole)+, i.e. (CHDT)+ and the like. The invention not only provides in pure form the organic halide compounds of variable, nonintegral stoichiometry where the halide presence is subvalent, but also includes compositions comprised of double salts of these organic cations, mixed or in combination with a single-valent transition metal ion. Preferred compositions have a preponderance of one of the organic cations with a minority, if any, of one or more of the other cations excluding a single-valent transition metal.

The compositions can be simple mixtures of the above crystalline compounds, as well as compositions in the form of a crystalline product where individual multiple halide anions and/or cations are present in the same crystal lattice. Preparation of a composition composed of different crystalline compounds by crystallization from a solution will result in the formation of a crystalline product where individual crystals contain a mixture of multiple subvalent halide anions and/or cations present, or a mixture of crystals of the individual compounds.

In addition to the above described compounds and compositions thereof, homologs and other simple derivatives of the compounds can also be employed, either as impurities in small quantity with the unsubstituted compound, as principal components of a composition, or as a pure compound. Suitable substituents include monovalent hydrocarbon groups such as methyl, ethyl, vinyl and phenyl groups and halogens such as chloro or bromo groups.

The compounds and compositions of this invention can be prepared by combining two or more electrically neutral reactants, or by combining two or more reactants which contain one or more of the desired ions. This can be accomplished by combining electrically neutral compounds such as (TTF) and liquid bromine in an appropriate medium to produce (TTF)$_m$(Br)$_n$ where ms is 1 and n is at least 0.001 and <1, and more preferably about 0.5 to about 0.9. Alternatively, a compound containing one of the ions in its ionic form such as (TTF)+ is combined with an appropriate transition metal salt and then reacted with an electrically neutral compound or with another ionic salt which can supply the necessary halide for creating the compounds of this invention. For the purpose of this invention, halide will preferably be defined to include only chloride, bromide, and/or iodide. The materials containing the desired compound components are usually brought together in the presence of a suitable solvent for the reactants such as acetonitrile, methylene chloride or acetone or a mixture of solvents such as acetonitrile-methanol, acetone-water-methanol and the like. Through contact of neat reactants, such as can be attained in the vapor phase, in the absence of any solvent or dispersing medium can also be used to form the compounds or compositions of this invention. If the reactants are salts having ions, e.g., barium or hexafluoroantimonate, which are not to become part of the compounds or compositions of this invention, the reaction mixture can be purified through crystallization or other known techniques to remove the byproducts of the reaction. Reaction temperatures are usually about 0° to 150° C., preferably about 20° to 80° C. For convenience it can vary considerably depending upon the thermal stability of the reactants and the time allotted for the reaction. One suitable combination of reaction time and temperature which has been employed because of its convenience has been 20° to 25° C. for two or three days. The two or three day reaction period is principally a matter of convenience, however, and can be shortened considerably with little or no loss in yield.

The compounds and compositions of this invention are useful as electrical conductors and for light polarization. Because of their advantageous combination of properties such as thermal and electrical conductivities and thermoelectric power coefficient, they are particularly useful as thermoelectric elements in thermoelectric devices. Compacted crystals of compounds or compositions of this invention have electrical conductivities at least an order of magnitude higher than conductivities reported in the prior art. Similarly, compounds of compositions of this invention in single crystal form also exhibit higher electrical conductivities than reported in the prior art for single crystals of related compounds.

EXAMPLE 1

Tetrathiofulvalene subchloride is prepared by dissolving tetrathiofulvalene monochloride hydrate (three parts) in hot acetonitrile solution together with tetrathiafulvalene (one part). This homogeneous solution is quickly filtered and allowed to cool, during which process crystals of the nonstoichiometric tetrathiafulvalene subchloride (formula: $C_6H_4S_4Cl_{0.72-0.77}$) grow in the flask.

The crystals appear as long black needles, typically 5–10 mm long, up to 1 mm square and have a room temperature conductivity of 90±10 ohm$^{-1}$cm$^{-1}$.

Crystal Data: Tetragonal crystals, a=15.63 Å, C=3.56 Å, z=4; D meas.=1.75±0.01, D calc. for $C_6H_4S_4Cl_{0.74}$=1.72 gm cm$^{-3}$.

EXAMPLE 2

Tetrathiafulvalene sub-bromide is prepared by dissolving tetrathiafulvalene (seven parts) in hot acetonitrile approximately one gram in six liters. To this solution is added two and one-half parts liquid bromine, causing a color change from yellow to red. The solution is quickly filtered and allowed to cool slowly, during which time crystals of the product grow.

Analysis: Calculated for $C_6H_4S_4Br_{0.77}$:27.10%C; 1.62%H; 48.24%S; 23.14%Br. Found: 26.94%C;

1.30%H; 23.26%BR. (Calculated for C₆H₄S₄Br: 25.35%C; 1.42%H; 45.12%S; 28.11%Br.)

Crystal Data: Monoclinic, space group P2₁/a; a=46.77, b=15.59, c=24.92, B=91.3, Z=12. The crystalline product had a room temperature conductivity of about 100 ohm⁻¹ cm⁻¹.

EXAMPLE 3

Tetrathiafulvalene subiodide is prepared by the following procedure:

Tetrathiafulvalene iodide, a poorly crystalline solid of uncertain composition, is prepared by allowing equimolar quantities of tetrathiafulvalene and iodine to react in methylene chloride or chloroform solution, from which it precipitates. On dissolution of this solid in hot acetonitrile solvent, a red solution results, from which black needles, comparably deficient in iodine, crystallize. Twice repeating this procedure yields crystals of constant composition.

Analysis: Calculated for C₆H₄S₄I₀.₇₂ 24.43%C; 1.37%H; 30.73%I. Found: 24.46%C; 1.35%H; 31.45%I.

Crystal Data: Monoclinic crystals, space group P2₁/a; a=48.17, b=16.05, c=24.94 Å, B=91.13, Z=12. Measured density 2.132; calculated for C₆H₄S₄I₀.₇₂, 2.134 gm cm⁻³. The crystalline product had a room temperature conductivity of 150±50 ohm⁻¹ cm⁻¹.

EXAMPLE 4

Tetrathiafulvalene Copper Chloride is prepared by the following procedure:

Tetrathiafulvalene (five parts) and anhydrous cupric chloride (two parts) are dissolved in refluxing acetonitrile (about 1 gm per liter). On cooling, reddish-black, needle-like crystals grow.

Analytical Data: The following results found by X-ray microprobe fluorescence: 51.7±1.6%S; 4.3±0.5% Cu; 8.4±0.7% Cl; indicating a subvalent salt of TTF.

Crystal Data: Tetragonal crystals, space group P4n2; a=11.171, c=3.646 Å; D meas=1.861 gm cm⁻³.

The crystalline product had a room temperature conductivity of 125±50 ohm⁻¹cm⁻¹.

EXAMPLE 5

Tetrathiafulvalene copper bromide is prepared by the following procedure:

Tetrathiafulvalene (five parts) and anhydrous cupric bromide (two parts) are dissolved together in hot acetonitrile (approximately 1.2 gm per liter). The resulting dark red solution is filtered and allowed to cool slowly to room temperature. Black, needlelike crystals isostructural with the analogous copper-chloride compound, are isolated.

Analytical Data: The following results found by X-ray fluorescence: 1-10%Cu,>10%S; indicating a subvalent salt of TTF.

EXAMPLE 6

Hypothetically tetraselenofulvalene sub-bromide is prepared by the following procedure:

Tetraselenofulvalene (ten parts) is dissolved in hot acetonitrile, approximately 0.25 gm per liter, and treated with solid gold tribromide (one part). The resulting deep purple-red solution is quickly filtered and allowed to cool, during which time black, needle-like crystals grow.

What is claimed is:

1. Subvalent organic halide compounds having the formula

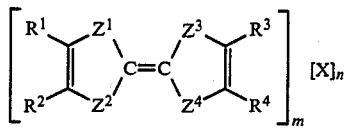

where m is equal to 1 and n is a positive number of from about 0.5 to about 0.9; R¹, R², R³ and R⁴ are each independently selected from the group consisting of hydrogen, or a normal alkyl group having 1 to 7 carbon atoms per group, Z¹, Z², Z³ and Z⁴ are either all sulfur or all selenium and x is at least one of chlorine, iodine, or bromine; and the compounds are electrical conductors at room temperature.

2. Compounds according to claim 1 wherein R¹, R², R³, and R⁴ are all hydrogen.

3. Compounds according to claim 1 wherein Z¹, Z², Z³, and Z⁴ are sulfur.

4. Compounds according to claim 1 wherein Z¹, Z², Z³, and Z⁴ are all selenium.

5. Compounds of claim 1 which Z¹, Z², Z³ and Z⁴ are all sulfur and R¹, R², R³ and R⁴ are all hydrogen.

6. Compounds of claim 1 in which n is in the range of about 0.7 to 0.8.

7. Double cation subvalent halide compounds having the formula:

where (O) is the organic cation having the formula:

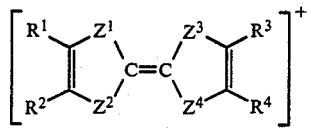

R¹, R², R³, and R⁴ are each independently selected from the group consisting of hydrogen, or a normal alkyl group having from 1 to 7 carbon atoms per group; Z¹, Z², Z³ and Z⁴ are either all sulfur or all selenium; (M) is copper; (X) is at least one of chlorine, bromine, or iodine; a is an integer of one or more; b is a positive number less than c, and the integer a is greater than c-b and the compounds are electrical conductors at room temperature.

8. Compounds according to claim 7 in which Z¹, Z², Z³ and Z⁴ are all sulfur.

9. Compounds according to claim 8 in which (X) is chlorine.

10. Compounds according to claim 8 in which X is bromine.

11. Compounds according to claim 3 in which R¹, R², R³ and R⁴ are all the same.

12. Compounds according to claim 4 in which R¹, R², R³ and R⁴ are all the same.

* * * * *